(12) United States Patent
Matusch

(10) Patent No.: US 9,717,853 B2
(45) Date of Patent: Aug. 1, 2017

(54) CYLINDER-PISTON UNIT WITH ADHESIVE DISC I

(71) Applicant: Rudolf Matusch, Marburg (DE)

(72) Inventor: Rudolf Matusch, Marburg (DE)

(73) Assignee: LTS LOHMANN THERAPIE-SYSTEME AG, Andernach (DE)

( * ) Notice: Subject to any disclaimer, the term of this patent is extended or adjusted under 35 U.S.C. 154(b) by 530 days.

(21) Appl. No.: 14/276,365

(22) Filed: May 13, 2014

(65) Prior Publication Data

US 2014/0243740 A1 Aug. 28, 2014

Related U.S. Application Data

(63) Continuation-in-part of application No. PCT/EP2012/072737, filed on Nov. 15, 2012.

(30) Foreign Application Priority Data

Nov. 16, 2011 (DE) .......................... 10 2011 119 058

(51) Int. Cl.
*A61M 5/30* (2006.01)
*A61M 5/24* (2006.01)
(Continued)

(52) U.S. Cl.
CPC ................ *A61M 5/30* (2013.01); *A61M 5/24* (2013.01); *A61M 5/3134* (2013.01);
(Continued)

(58) Field of Classification Search
CPC ........ A61M 5/24; A61M 5/30; A61M 5/3134; A61M 2005/3118; A61M 2005/2013; A61M 2005/2488; A61M 5/31513
See application file for complete search history.

(56) References Cited

U.S. PATENT DOCUMENTS 6,213,977 B1 4/2001 Hjertman et al.
6,890,319 B1 5/2005 Crocker
(Continued)

FOREIGN PATENT DOCUMENTS

DE 698 36 594 T3 5/2010

*Primary Examiner* — Theodore Stigell
(74) *Attorney, Agent, or Firm* — R. S. Lombard

(57) ABSTRACT

A cylinder-piston unit of a needle-free injector, with at least one cylinder accommodating an injection solution, at least one piston, and an adhesive coating arranged in the area of the free end face of the cylinder. The cylinder has a bottom portion, on which a discharge tube is arranged. An adhesive disc, which is displaceable in the direction of the center line of the cylinder-piston unit between an installation position and an application position, is arranged on the discharge tube and/or on the bottom portion. The adhesive disc has an adhesive coating on each of the two end faces. In the installation position, the discharge tube can be sealed off in the adhesive disc. In the application position, the front edge of the discharge nozzle lies in the plane of the front adhesive coating or protrudes beyond this plane by at least 0.5 mm. A needle-free cylinder-piston unit of an injector whose discharge system is suitable for safely penetrating the outer layers of skin, covered by the term "dermis", in order to convey the injection solution into or under the skin.

6 Claims, 5 Drawing Sheets

(51) Int. Cl.
   *A61M 5/31*     (2006.01)
   *A61M 5/315*    (2006.01)
   *A61M 5/20*     (2006.01)

(52) U.S. Cl.
   CPC . *A61M 5/31513* (2013.01); *A61M 2005/2013* (2013.01); *A61M 2005/2488* (2013.01); *A61M 2005/3118* (2013.01)

(56) References Cited

U.S. PATENT DOCUMENTS

| | | |
|---|---|---|
| 9,415,166 B2 * | 8/2016 | Matusch ............ A61M 5/3007 |
| 2002/0193740 A1 | 12/2002 | Alchas et al. |
| 2003/0014006 A1 | 1/2003 | Alexandre et al. |
| 2007/0021716 A1 | 1/2007 | Hansen |
| 2008/0287885 A1 | 11/2008 | Hoffmann et al. |
| 2009/0099510 A1 | 4/2009 | Poulsen |
| 2009/0227942 A1 * | 9/2009 | Stroem Hansen ...... A61M 5/30 604/68 |
| 2011/0155520 A1 | 6/2011 | Takahashi et al. |
| 2011/0214777 A1 | 9/2011 | Matusch |
| 2011/0270217 A1 | 11/2011 | Stroem Hansen et al. |

* cited by examiner

CYLINDER-PISTON UNIT WITH ADHESIVE DISC I

CROSS-REFERENCE TO RELATED APPLICATION

This is a continuation-in-part application of pending international application PCT/EP2012/072737 filed Nov. 15, 2012 and claiming the priority of German Application No. 10 2011 119 058.2 filed Nov. 16, 2011 which is hereby incorporated herein by reference in its entirety as though fully set forth.

BACKGROUND OF THE INVENTION

The invention relates to a cylinder-piston unit of a needle-free injector, with at least one cylinder accommodating an injection solution, at least one piston, and an adhesive coating arranged in the area of the free end face of the cylinder.

DE 10 2005 054 600 discloses a cylinder-piston unit of a needle-free injector, of which the cylinder has, at its front end face, a sealing film fixed by means of a pressure-sensitive adhesive. The pressure-sensitive adhesive has a greater affinity to the end face of the cylinder than to the sealing film, such that, after the sealing film has been pulled off, the pressure-sensitive adhesive remains in place in order, during the injection, to fix the skin of the patient with respect to the injector.

DE 698 36 594 T3 describes a device for transcutaneous placement of a flexible cannula at a medicament admission site on the patient. For this purpose, the device has an adapter set, and a spring accumulator that can be tensioned and that is accommodated in a housing. The adapter set, which can be inserted from the front into the housing, is principally composed of an adhesion plate, a flexible cannula and an insertion needle. When the device is triggered, the adapter set is positioned on the skin by means of the relaxation of the spring accumulator. The cannula is pushed under the skin with the aid of the insertion needle. After the housing has been removed and the insertion needle pulled out, the infusion can begin.

In needle-free injections, the injection solution must be administered by a high-velocity jet through the skin of the patient. The upper layer of the skin constitutes a strong mechanical covering of the skin layers lying below it and protects them from external influences. It is composed of keratinized cells which lie alongside and over one another, the interstices being lined by lipids.

In the context of a modular injector, the object of the present invention is therefore to develop a cylinder-piston unit whose discharge system is suitable for safely penetrating the outer layers of skin covered by the term "dermis", or possibly also the other layers, in order to convey the injection solution into or under the skin.

SUMMARY OF THE INVENTION

This object is achieved, according to the invention, by the features of claim 1. To this end, the cylinder has a bottom portion, on which a discharge tube is arranged. An elastic adhesive disc, which is displaceable in the direction of the centre line of the cylinder-piston unit between an installation position and an application position, is arranged on the discharge tube and/or on the bottom portion. The adhesive disc has an adhesive coating on each of the two end faces. In the installation position, the discharge tube can be sealed off in the adhesive disc. In the application position, the adhesive disc bears with adhesive bonding on the front end face of the bottom portion. In the application position, the front edge of the discharge nozzle lies in the plane of the front adhesive coating or protrudes beyond this plane by at least 0.5 mm.

Here, the cylinder-piston unit of a needle-free injector, for example, is proposed by the invention. The injector, which can also be a disposable injector, not only accommodates the cylinder-piston unit but also a drive mechanism that is installed in an injector housing and that acts on a piston-actuating ram. As possible drive mechanisms, it is possible to use spring accumulators, gas drives with openable gas cartridges, or pyrotechnic drives. Known spring energy accumulators use pretensioned mechanical or pneumatic springs or spring systems. If a spring energy accumulator is used as drive mechanism, the piston-actuating ram is held with a form fit, via at least one support rod or draw hook arranged on or in the injector housing, in order to pretension and hold this spring energy accumulator. The one or more support rods or draw hooks are retained in their locked position by means of one or more trigger elements until the use of the injector. To trigger the injector, the one or more support rods or draw hooks are released, such that the piston-actuating ram, under the effect of the spring energy accumulator, can move at least approximately parallel to the centre line of the injector, with the result that the injection solution present in the cylinder of the cylinder-piston unit is expelled via at least one nozzle.

In the present case, an adhesive disc, displaceable on the cylinder, is mounted in front of the cylinder-piston unit. When the ready-to-use injector is placed onto the skin of the patient, the skin of the patient adheres, in a first step, to the adhesive disc sitting on the cylinder in an installation position. By further pressing the injector onto the skin, the adhesive disc slips, if appropriate with the adhesive disc being pushed open or pierced.

At the same time, the displacement of the adhesive disc causes a partial stretching of the skin in the injection area. Depending on the lifting travel of the adhesive disc, the tensioning of the upper layer of skin in the area of the outlet nozzle leads to a one-stage or two-stage pulling-apart of the keratinized cells of the horny layer of the skin. The first or single stage involves the widening of the central bore of the elastic adhesive disc and, therefore, the tensioning of the skin covering the bore. This first stage ends when the front end of the nozzle of the discharge tube comes to a stop at the level of the front end face of the adhesive disc.

The second or additional stage involves an indentation of the skin by further displacement of the adhesive disc in the range of tenths of a millimeter. The indentation results from the protrusion of the front end of the discharge tube beyond the adhesive disc. The indentation thus causes an additional stretching of the skin. Both stages facilitate the penetration of the injection jet during the administration.

BRIEF DESCRIPTION OF THE DRAWINGS

Further details of the invention will become clear from the dependent claims and from the following descriptions of schematically depicted illustrative embodiments.

DETAILED DESCRIPTION OF THE PARTICULAR EMBODIMENTS

Figure 1:
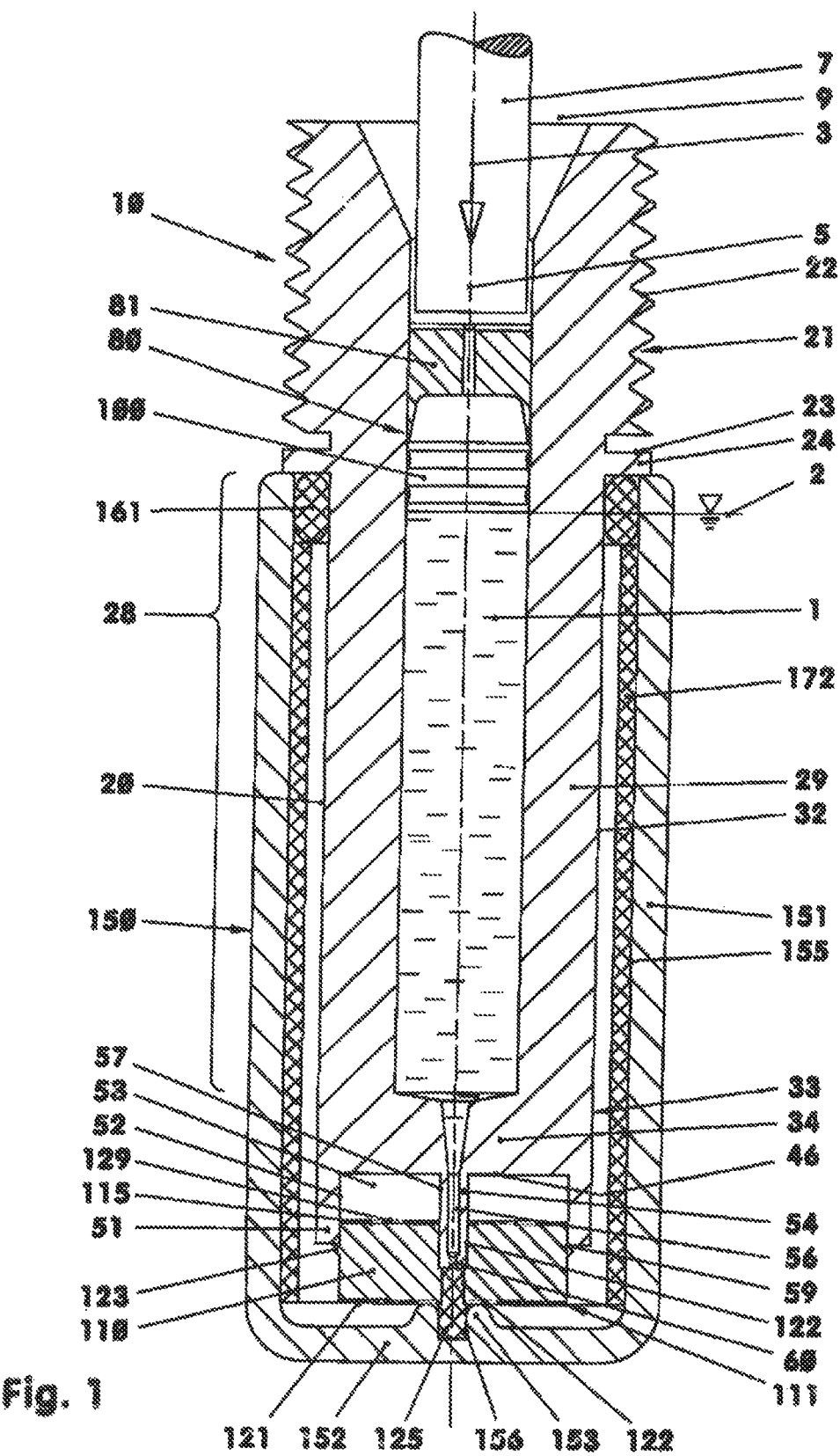
FIG. 1 shows a cylinder-piston unit with integrally formed discharge tube and protective housing.

FIG. 1 shows a cylinder-piston unit (10) of a needle-free injector. The cylinder-piston unit (10) is composed of a cylinder (20) and a piston, for example a two-part piston (80). The cylinder (20) is additionally surrounded, for example, by a protective housing (150). Above the piston (80), the lower part of a piston-actuating ram (7) is shown, which belongs to the injector (not depicted here). The cylinder (20) is secured on the injector by means of its outer thread (22), present in the rear area of the cylinder, or by means of slits (23). In the area of the cylinder bottom, a double-sided adhesive disc (110) is also arranged between the cylinder (20) and the protective housing (150).

The for example one-part cylinder (20) is composed of a housing adapter (21), a tube portion (28) and a bottom portion (33). With the housing adapter (21), the cylinder (20) is fixed in an injector housing (not depicted). For this purpose, its radial outer wall has an outer thread (22) and/or at least two slits (23) lying opposite each other. The slits (23) have a depth of 2 mm, for example. They are located at the thread end in immediate proximity to the tube portion (28). The width of the slits (23) is 0.6 mm, for example.

Between the slits (23) and the tube portion (28), there is an abutment web (24), of which the external diameter can be identical, for example, to the outer diameter of the thread. The external diameter of the tube portion (28) is more than twice as great as the diameter of the inner wall (31). It is dimensioned such that its material withstands at least a pressure load of $350*10^5$ Pa (pascals).

The housing adapter (21) is adjoined by the cylinder wall (29) of the tube portion (28). Along the length of the tube portion, the cylinder wall (29) has, for example, a constant wall thickness of 3.25 mm.

The bottom portion (33) has an outwardly plane bottom plate (34), which corresponds to the mean wall thickness of the cylinder wall (29) in the area of the tube portion (28). An annular web (51), e.g. in the shape of a cylindrical tube, is integrally formed in the outer area of the bottom plate (34). The annular web (51), which encloses a receiving space (53) for the adhesive disc, is, for example, as high as the wall thickness of the bottom plate (34). The wall thickness of the annular web (51) is about one third of the wall thickness of the cylinder wall (29) of the tube portion (28).

The discharge tube (54) supporting the outlet nozzle (60) is arranged in the centre of the plane bottom plate (34). The discharge tube (54), of which the external diameter measures 2.25 mm for example, has a front end which protrudes about one millimeter beyond the annular web (51). Lying between the at least approximately cylindrical outer wall of the discharge tube (54) and the cylindrical inner wall (52) of the annular web (51), there is a receiving space (53), e.g. with a depth of 3 mm, for the adhesive disc. Instead of the integrally formed discharge tube (54), it is also possible to use a thin-walled tube (55) (cf. FIG. 2), at the front end of which an outlet nozzle (60) is arranged. The thin-walled tube (55), which is produced for example from a stainless steel, has an external diameter of 0.5 mm, for example. The wall thickness of the discharge tube (55) behind the outlet nozzle (60) measures 0.05 mm, for example. The nozzle diameter, or the internal diameter of the discharge tube (55), generally corresponds to the values known from the previous variant. According to FIGS. 2, 5, 6 and 7, the internal diameter measures 0.2 mm for example, while the external diameter measures 0.36 mm. In order to produce this outlet nozzle (60), the front area of the discharge tube (55) is reduced to a length of ca. 0.325 mm by material compression, such that a tapering (63) is obtained directly behind the outlet nozzle (60).

The free nozzle end is rounded with a radius of 0.05 mm, for example, so as not to damage the skin (200) during use.

According to FIG. 1, an adhesive disc (110) is arranged between the discharge tube (54) and the annular web (51), in the front area of the receiving space (53) for an adhesive disc. It has a material thickness that is at least 0.5 mm greater than the depth of the receiving space (53) for the adhesive disc. The adhesive disc (110) has a central bore (122), of which the internal diameter is smaller, e.g. by 0.5-1 mm, than the external diameter of the discharge tube (54). Thus, the front area of the discharge tube (54) is surrounded tightly and sealingly by the rear area of the bore (122). The front and still unexpanded area of the bore (122) thus appears in FIG. 1 with a smaller diameter.

For the cylinder variant with the cemented-in or encapsulated discharge tube (55), an adhesive disc (110) is used that has no bore. According to FIG. 2, the area of the adhesive disc (110) located in front of the discharge tube (55) is identified as a sealing area (117).

The substantially cylindrical outer wall of the adhesive disc (110) is guided on the cylindrical inner wall (52) of the annular web (51). According to FIG. 1, the adhesive disc (110) has, in the upper area of its outer wall, a circumferential web (123) which protrudes radially, e.g. by 0.5 mm, and via which the adhesive disc bears elastically on the front inside edge (59) of the annular web (51).

For positioning the adhesive disc (110) on the annular web (51) of the bottom portion (33), the latter can also have a radially inwardly protruding web, which is integrally formed in the front area of the annular web (51) and which protrudes elastically into a corresponding annular groove of the adhesive disc (110).

The adhesive disc (110) is made of rubber, for example, or of another elastomer and is provided, on both its, for example plane, end faces, in each case with an adhesive layer (121, 129) composed, for example, of a pressure-sensitive adhesive. The rest of the surface areas have good sliding ability, since the adhesive disc (110) is at least partially treated with silicone oil or coated with Teflon. In the variant suitable for the discharge tube (54) (cf. FIGS. 1, 3 and 4), the adhesive layer (121) is omitted in the area of the bore (122). In the variant for the metallic discharge tube (55), the adhesive layer (121) can have a central recess (124), of which the diameter is at least greater than the external diameter of the discharge tube (55) in the area of the outlet nozzle (60) (cf. FIG. 6).

The pressure-sensitive adhesive of the adhesive disc (121) is such that its adhesion force with respect to the adhesive disc (110) is at least 50% greater than with respect to a disinfected skin surface (201).

Figure 4:
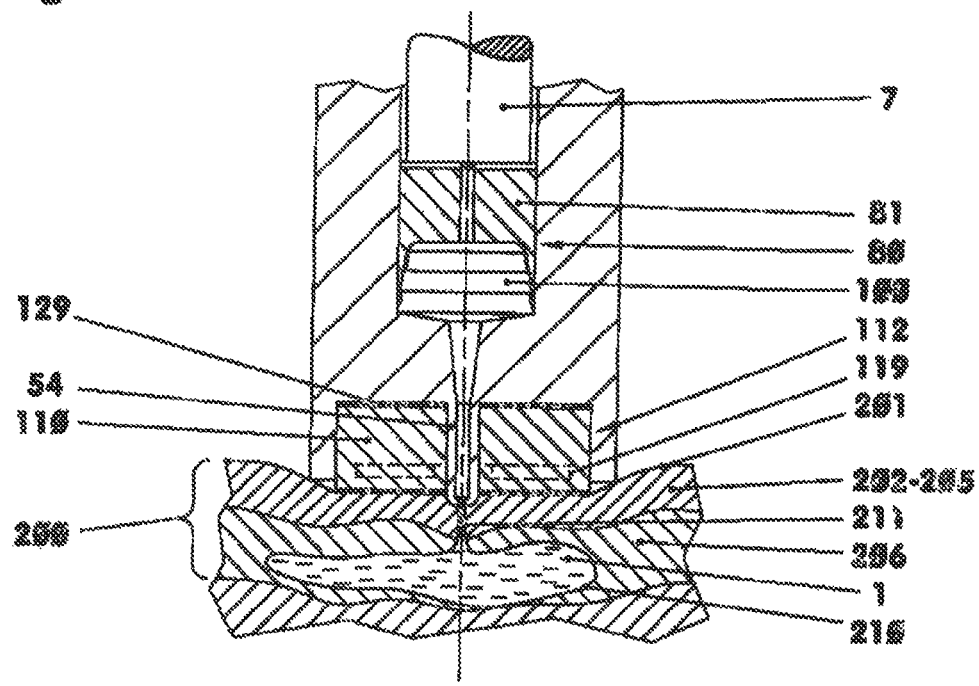
FIG. 4 shows the same as FIG. 3, but with a long discharge tube.

A stiffening disc (119) can be inserted into the adhesive disc (110). It is shown in FIG. 4 by broken lines. This stiffening disc (119), e.g. encapsulated or vulcanized in, has a wall thickness of 0.5-1 mm, for example. It is made from a conventional ferrous or non-ferrous metal, for example. Its bore is at least 1 mm larger than the external diameter of the discharge tube (54). The external diameter of the stiffening disc (119) is, for example, 1-2 mm smaller than the external diameter of the adhesive disc (110). The stiffening disc (119), here integrated into the adhesive disc (110), is positioned for example 0.5 to 1 mm behind the front adhesive layer (121). The centre lines of the adhesive disc (110) and of the stiffening disc (119) are congruent.

If appropriate, the adhesive disc (110) has at least one lateral notch, which is oriented parallel to the centre line (5) and by means of which, upon insertion of the adhesive disc (110) into the receiving space (53), the air present therein can be easily displaced. The air can also escape via a bore arranged in the annular web (51), in proximity to the end face (46) of the bottom portion (33).

According to FIG. 1, the pot-shaped protective housing (150), a sterile closure, which is made of glass for example, here consists of a tubular jacket (151) and of a plane bottom (152). The cylindrical, smooth outer wall (32) of the tube portion (28) and of the bottom portion (33), with the inserted adhesive disc (110), of the cylinder (20), is here surrounded by the protective housing (150). In the area of the tube portion (28), the distance between the outer wall (32) and the inner wall (155) of the protective housing (150) is 1.5 mm, for example. The axial distance between the bottom (152) of the protective housing (150) and the adhesive disc (110) measures 1 mm, for example, according to FIG. 1.

The protective housing (150) is fixed releasably on the cylinder (20) at two locations. The first location lies at the transition between the tube portion (28) and the abutment web (24) of the cylinder (20). There, according to FIG. 1, an O-ring (161) seals the protective housing (150) in relation to the cylinder (20). At the same time, the O-ring (161) centres the protective housing (150) on the cylinder (20). Instead of a conventional O-ring (161), it is also possible to use a quad ring, a profiled ring or the like.

Upon assembly, the sealing ring (161) is clamped between the protective housing (150) and the cylinder (20), such that, in addition to the sealing function, it can also easily perform a holding function. If appropriate, the sealing ring (161) can also be replaced by a tough sealing adhesive.

The second location for supporting the protective housing (150) on the cylinder (20) is situated centrally in the bottom (152) of the protective housing (150). There, a central blind bore (156) is arranged, which is surrounded by an inwardly protruding supporting web (153) formed integrally on the bottom (152). The annular supporting web (153) bears with its for example half-toric end face on the adhesive disc (110).

A stepped rubber stopper (125) is fitted in the blind bore (156) by clamping or adhesive bonding. The rubber stopper (125) sits sealingly with its rear end in front of the outlet nozzle (60) of the discharge tube (54). Its front end, engaged in the blind bore (156), has a diameter which is, for example, 0.5 mm greater than that of its rear end. The rubber stopper (125) fixes the front end of the protective housing (150) radially over the adhesive disc (110), which bears on the annular web (51) of the cylinder (20).

Figure 2:
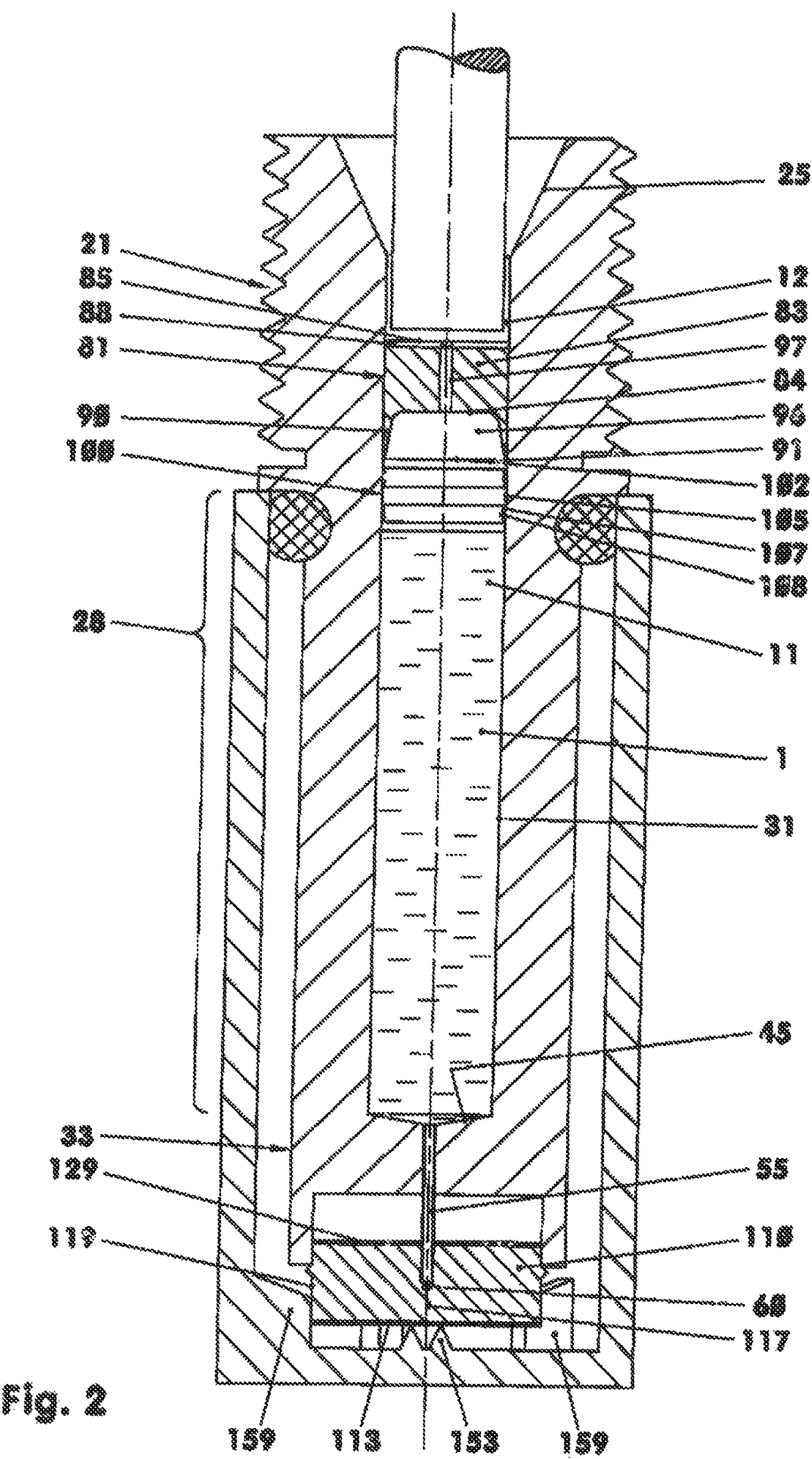
FIG. 2 shows the same as FIG. 1, but with a metallic discharge tube.

In the illustrative embodiment according to FIG. 2, the protective housing (150), on account of its shape, is made from the plastics material cyclo-olefin copolymer (COO). This material has a particularly low permeability to gas and water vapour.

To be able to support the protective housing (150) in the front area on the cylinder (20) also in the radial direction in the variant, the protective housing (150) has, for example, five radially oriented supporting ribs (159). These supporting ribs (159), distributed equidistantly on the circumference of the jacket (151), are, for example, integrally formed on the bottom (152) and on the jacket (151). The supporting ribs (159) have radial inner faces via which they bear on the cylindrical outer face (119) of the adhesive disc (110).

For axial support of the adhesive disc (110), the bottom (152) is additionally provided with an annular supporting web (153), which bears with its upper circular edge on the adhesive disc (110), in the edge region of the latter. The edge is so narrow that it develops only a slight adhesion force with respect to the adhesive disc (110).

According to FIGS. 1 and 2, the cylinder (20) is at least partially filled with an injection solution (1). The liquid level (2) of the injection solution (1) is situated in the transition area between the housing adapter (21) and the tube portion (28). A disc-shaped sealing body (100) is placed on the liquid level (2) in a sterile manner and without bubbles and, under the effect of radial clamping, bears sealingly on the inner wall (31) of the cylinder. A pot-shaped drive body (81) is arranged behind the sealing body (100). The drive body (81) bears partially on the sealing body (100) or is at a distance of, for example, 0.2 to 0.5 mm therefrom.

The sealing body (100) here is a disc whose undeformed diameter is, for example, twice as great as its disc thickness. On its circumference, the disc (100) can have a grooved profile (107) with, for example, two grooves (108) (cf. FIG. 2). The grooved profile (107) is, for example, configured here such that the sealing body (100) has, in cross section, a wave line with two wave valleys forming the grooves (108). The wave line is composed here of arcs of a circle.

Since the sealing body (100) is an elastomer body, the wave crests of the sealing disc are flattened off (cf. FIGS. 1, 2, 3, 4 and 5).

The pot-shaped drive body (81), whose length corresponds to its external diameter for example, is composed of a disc-shaped impact plate (83) and of a skirt (90) formed integrally thereon. The thickness of the impact plate (83) is here slightly greater than the length of the skirt (90) (cf. FIG. 2).

The impact plate (83), which is impacted by the piston-actuating ram (7) when the injector is triggered, has at least a for example central bore (97), by which the cylinder chamber areas (11, 12) located in front of and behind the drive body (81) are connected to each other with minimal restriction. According to the illustrative embodiments, the bore (97), which can also be oriented obliquely with respect to the centre line (5) and of which the minimum diameter is between 1 and 2 mm, ends on the rear face (85) of the drive body (81), e.g. in a channel intersection (88) composed of two channels intersecting in the area of the bore (97). The channels of the channel intersection (88) each have a semi-circular cross section, wherein the diameter of the cross sections corresponds, for example, to the diameter of the bore.

The front face (84) of the impact plate (83) is adjoined by the skirt (90), which is designed as an elastic sealing lip. Starting from the front face (84), the wall of the skirt (90) tapers towards the front outer sealing edge (91), which bears elastically on the inner wall (31) of the cylinder in each operating state of the injector. In the installed state, the skirt

(90) and the front face (84) enclose an immersion space (96). The latter has substantially the shape of a truncated cone, of which the cone angle measures 20 degrees, for example.

The piston (80), i.e. the combination of the drive body (81) and of the sealing body (100), permits simple bubble-free, sterile filling and a closure of the cylinder-piston unit (10) in connection with an ejection procedure upon release of the injector, which withstands a very high compression pulse of up to $350*10^5$ Pa.

When the injector is ready for the injection, the protective housing (150) is pulled off from the front of the cylinder (20), e.g. by manual force.

When the injector is ready for the injection, the protective housing (150), together with the cotton woven fabric (172), is pulled off from the front of the cylinder (20), e.g. by manual force. In doing this, in the variant according to FIG. 1, the rubber stopper (125) remains attached to the protective housing (150), while the sealing ring (161) remains on the outer wall (32) of the cylinder (20). The adhesive disc (110) stays in the bottom portion (33) of the cylinder (20), in the position known from FIG. 1.

To be able to administer the injection solution, the injector, with the adhesive disc (110) towards the front, is placed onto the skin surface (201) of the patient. The adhesive disc (110), which is still located in its installation position (111), affixes itself to the skin surface (201) via its adhesive layer (121) which, for example with a diameter of 10 mm, has a surface area of ca. 75 mm².

By means of the pressing force of the injector, the adhesive disc (110) is loaded in such a way that, with the locking action of the circumferential web (123) being overcome, it is moved along the discharge tube (54) in the direction of the bottom portion (33). While the front end face (58) of the discharge tube (54) moves towards the skin, the discharge tube (54) expands the front blind bore by ca. 0.5 mm. This expansion has the effect that the layer of skin affixed to the adhesive layer (121) is actively tensioned in a first, if appropriate single, stage, solely by the widening of the blind bore (126). The expansion factor is the quotient of the square of the external diameter of the discharge tube (54) and the square of the internal diameter of the still unexpanded bore (122).

Figure 3:
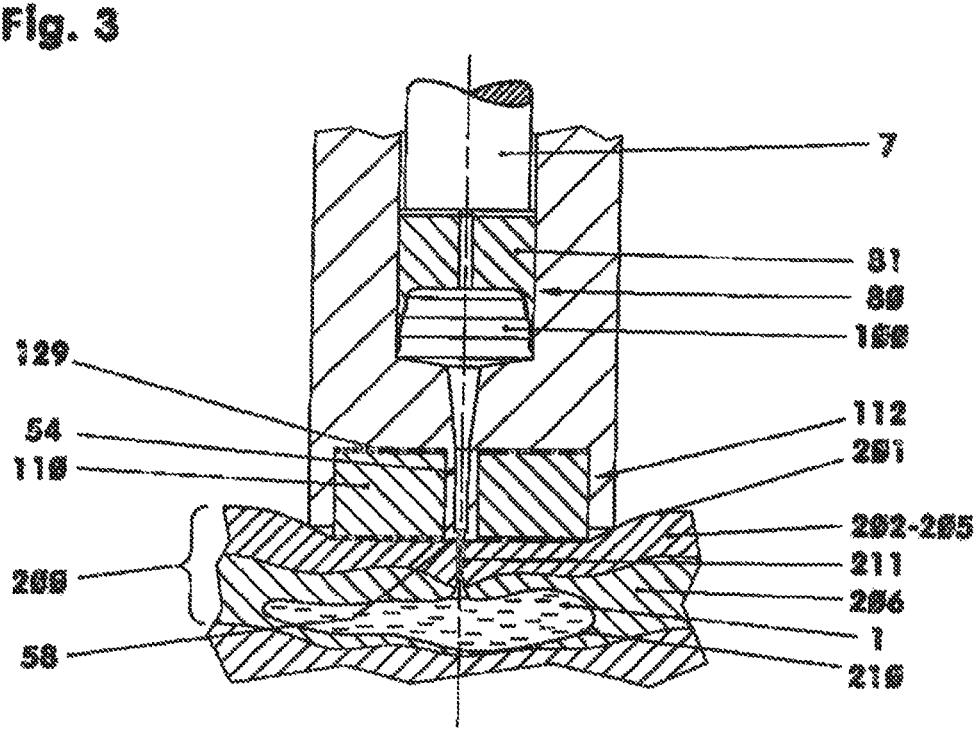
FIG. 3 shows a cross section through the front area of the cylinder-piston unit with integrally formed short discharge tube, after the injection solution has been dispensed.

If the skin (200) is to be stretched only in one stage, the lifting travel of the adhesive disc (110) is chosen, through the geometric matching of the height of the annular web (51) or the length of the discharge tube (54) and the wall thickness of the adhesive disc (110), such that the front edge (61) of the outlet nozzle (60) of the discharge tube (54, 55) lies at least approximately in the plane which is to be regarded as the front end plane of the front adhesive layer (121). In FIG. 3, the shortened discharge tube (54) has, for example, a plane end face (58), which specifically comes to a stop in this plane.

Since the adhesive layer (121) generally has a very thin wall, it suffices if the end face (58) is located anywhere between the rear end face and the front end face of the adhesive layer (121).

After completion of the first stage, the adhesive disc (110) bears with its rear adhesive layer (129) on the end face (46) of the bottom portion, whereupon the dispensing of the injection solution (1) can be initiated.

As an alternative to this, the stretching of the skin (200) can take place in two stages. The first stage described in the previous section is supplemented by a second, which is initiated by a further displacement of the adhesive disc (110). In this case, there is still play of a few tenths of a millimeter between the adhesive disc (110) and the end face (46).

In the subsequent forward movement of the injector, using the still existing play, the adhesive disc (110) slips further into the receiving space (53) for the adhesive disc, so as to bear with its rear face (115) on the end face (46) of the bottom portion (33). The adhesive disc (110) is now located in its application position (112). It now completely fills the receiving space (53) for the adhesive disc.

This second travel of the adhesive disc (110) means that, on the one hand, the adherence between the adhesive layer (121) and the skin of the patient is strengthened by the increased contact pressure, and, on the other hand, the discharge tube (54) protrudes a few tenths of a millimeter from the adhesive disc (110) (cf. FIG. 4).

The front end (58) of the protruding discharge tube (54), with the for example almost spherically curved front face (58), forces a depression into the skin (200), as a result of which the second stage of the skin expansion begins. The resulting indentation depth, which is the distance between the lower adhesive layer (121) and the most forward point or the most forward edge of the discharge tube (54), corresponds, for example, to half the external diameter of the discharge tube (54). In this case, the skin surface (201) in the area of the front face (58) of the discharge tube (54) is actively expanded in total by ca. 100%.

If the injector from FIG. 2 is used, there is in principle a comparable two-stage stretching of the skin as in the example according to FIG. 1. On account of the relatively slender discharge tube (55) with its tapering (63) in the area of the outlet nozzle (60), there are, depending on the skin type, two different contact conditions for the skin (200) to be stretched.

In a first contact condition, when the discharge tube (55) emerges, the skin (200) nestles on the outer wall (57), such that the surface (201) of the stretched skin (200) assumes the shape of a stepped tin, wherein the stepped tin shape comes about through the tapering (63) of the discharge tube (55). In the two-stage skin expansion, this variant results, for example, in an expansion factor of 3.5 to 4.

In a second contact condition, the horny layer (203) is lifted away or detached from the adhesive layer (121) in part by the outlet nozzle (60), without damaging the skin (200). The lifting area has, for example, a diameter (207) that can measure up to 1 mm.

Figure 7:
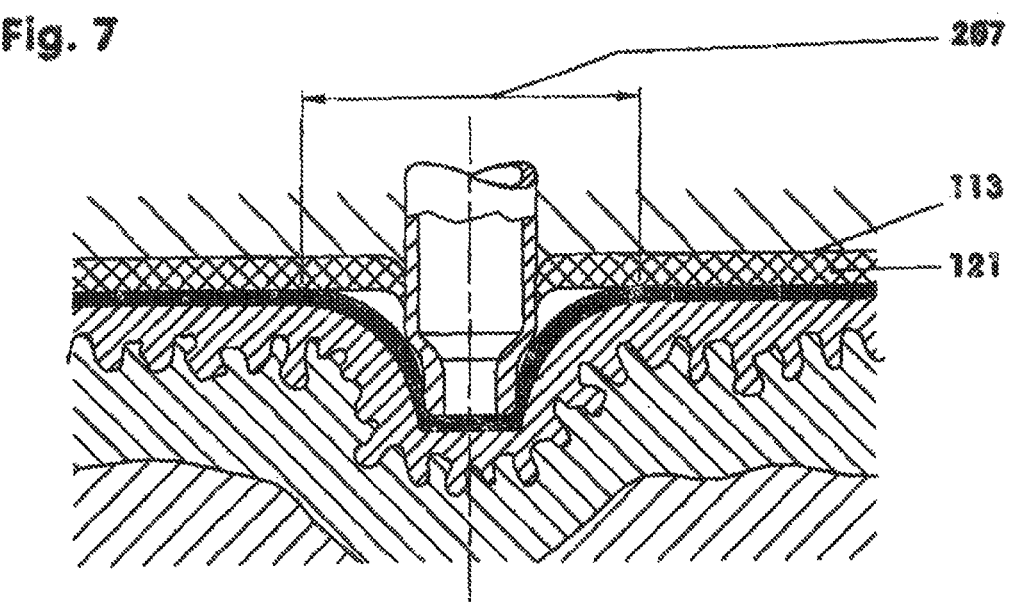
FIG. 7 shows the same as FIG. 6, but after complete piercing of the adhesive disc and tensioning of the patient's skin.

With greater expansion in the area around the outlet nozzle (6), the skin (200) will here assume a for example funnel-like configuration (cf. FIG. 7). Here, the epidermis (202) and the dermis (205) are indented into the subcutis (206). With the geometrical conditions according to FIG. 7, in which the indentation of the horny layer corresponds to about half the diameter (207) of the skin surface (201) detached from the adhesive layer (121), a horny-layer expansion of 60 to 70% is obtained there in the area of the funnel-like indentation.

At the end, chronologically speaking, of the one-stage or two-stage stretching of the skin, the injector is triggered by the pressure applied to it by the patient. The piston-actuating ram (7), pretensioned by means of a mechanical or pneumatic spring, applies a sudden load to the piston (80), such that the injection solution (1) penetrates in a high-velocity jet through the tensioned skin of the patient.

The piston-actuating ram (7) first strikes with great force against the drive body (81), see arrow direction (3) in FIG. 1. The drive body (81) is pressed against the almost incompressible sealing disc (100) resting on the liquid level (2).

The skirt (90) slides along the inner wall (31) of the cylinder via the, for example profiled, outer wall (105) of the sealing disc (100). The sealing disc (100) enters the immersion space (96) of the drive body (81), cf. in this case FIGS. 3 to 5. The displaced air flows through the bore (97) and along the channel intersection (88) on the piston-actuating ram (7) into the external environment (9) of the injector.

The sealing disc (100) and the drive body (81) now form a virtually rigid combination, namely the piston (80), which pushes the injection solution (1) forwards. The sealing with respect to the inner wall (31) of the cylinder is taken over by the sealing edge (91) of the skirt (90), which is pressed on more strongly by the sealing disc (100) loaded by the pressure of the liquid. Since the coefficient of sliding friction of the sealing edge (91) is less than the coefficient of sliding friction of the sealing disc (100) because of the material used for the drive body, there is a low sliding-friction resistance despite the high sealing action.

Figure 5:
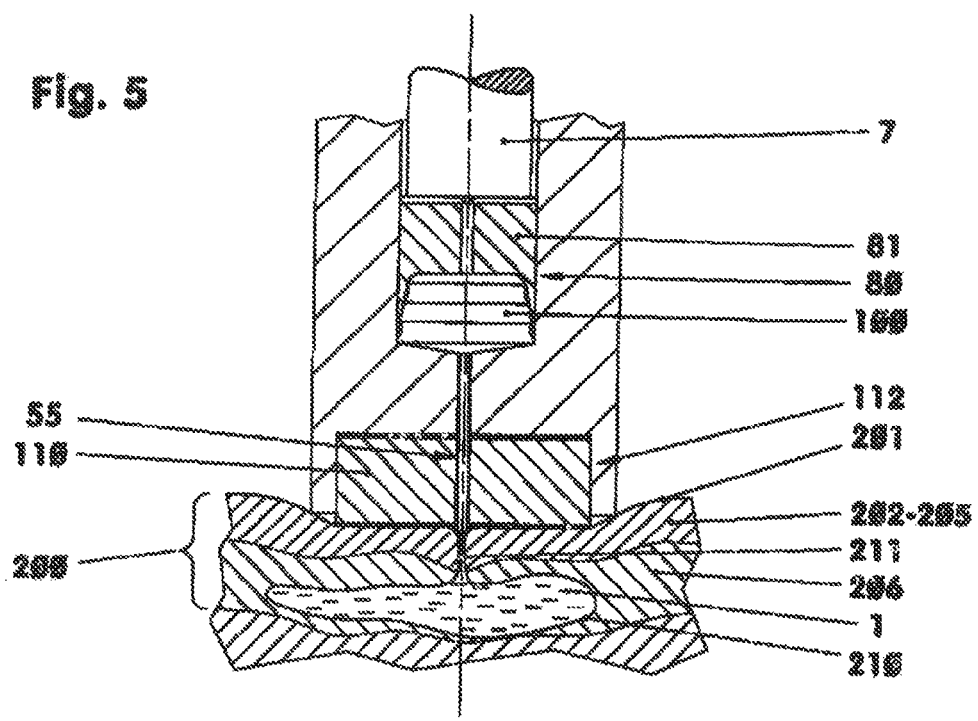
FIG. 5 shows the same as FIG. 4, but with a long metallic discharge tube.
Figure 6:
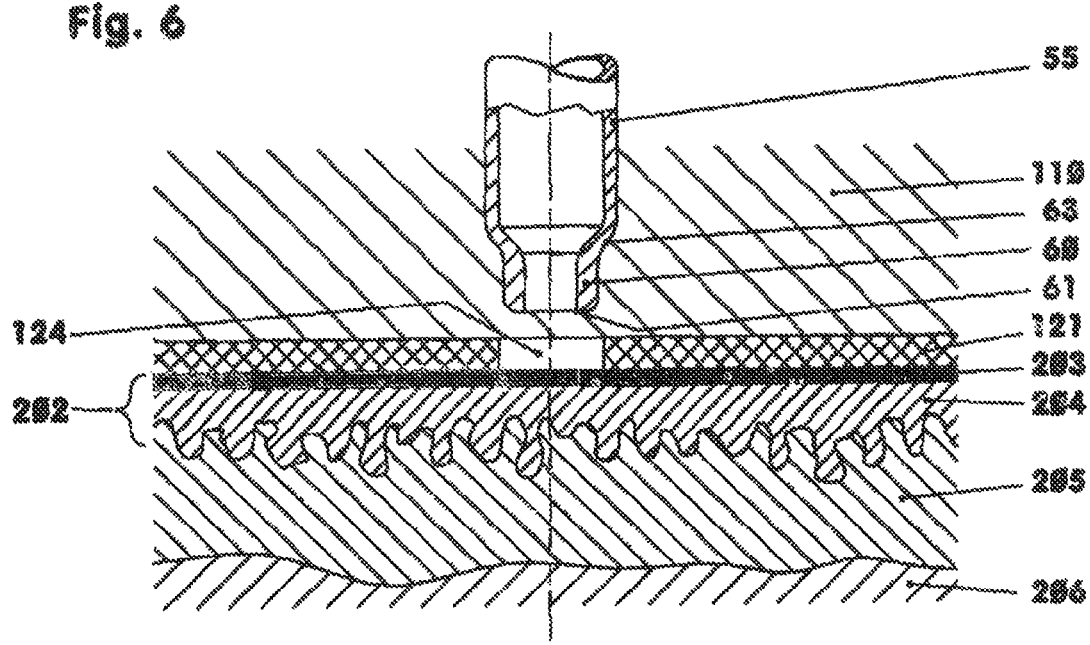
FIG. 6 shows a cross section of the metallic discharge tube after it has been placed onto the skin of the patient, before complete piercing of the adhesive disc.

As a result of the high pressure of the liquid which, for example for subcutaneous injection at a flow velocity of ca. 150 m/sec, measures at least $250*10^5$ Pa, the liquid jet penetrates the epidermis (202) and the dermis (205), which together are up to 2 mm thick for example (cf. FIGS. 3 to 5). In subcutaneous injection, an inflow channel (211) generated by the liquid jet ends only in the subcutis (206). In the connective tissue of the subcutis (206), which is permeated by capillary vessels and is rich in adipose tissue, a for example discus-shaped pool (210) of injection solution then forms, which is fed by the liquid jet.

After the cylinder (20) has been emptied, the injector is released from the skin (200). Since the adherence between the cylinder (20) and the adhesive disc (110) is in principle greater than between the adhesive disc (110) and the skin (200), this takes place without difficulty and without causing pain.

At least most of the pressurized pool (210) of injection solution is retained in the skin, since the stretching of the skin immediately decreases after the injector is taken away, and the inflow channel (211) is therefore closed again.

LIST OF REFERENCE SIGNS

1 Injection solution
2 Liquid level
3 Arrow direction upon injector release
5 Centre line
7 Piston-actuating ram
9 Environment
10 Cylinder-piston unit
11 Cylinder chamber area in front of the piston
12 Cylinder chamber area behind the piston
20 Cylinder
21 Housing adapter
22 Outer thread
23 Slits
24 Abutment web
25 Widening on the inside
28 Tube portion
29 Cylinder wall
31 Inner wall, radial
32 Outer wall, radial
33 Bottom portion
34 Bottom plate
45 Cylinder bottom, inner side of the cylinder bottom
46 End face of the bottom portion, front
51 Annular web
52 Inner wall, cylindrical
53 Receiving space for adhesive disc
54 Discharge tube, plastic
55 Discharge tube, tube, steel tube
56 Bore, inner bore
57 Outer wall
58 Face, end face
59 Front edge
60 Nozzle, outlet nozzle
61 Front edge
63 Tapering
80 Piston, combination of (81) and (100)
81 Drive body
83 Impact plate
84 Front face
85 Rear face
88 Channel intersection
90 Elastic skirt; sealing lip
91 Edge, sealing edge
96 Immersion space, hollow space
97 Recess, bore, central
100 Sealing body, sealing disc
102 Rear face
105 Outer wall, profiled
107 Grooved profile
108 Groove
110 Adhesive disc, elastomer disc
111 Installation position
112 Application position
113 Front face
115 Rear face
117 Sealing area
119 Outer face, radial
121 Adhesive layer, front, pressure-sensitive adhesive, adhesive coating
122 Stepped bore
123 Circumferential web
124 Recess in (121)
129 Adhesive layer, rear, pressure-sensitive adhesive, adhesive coating
150 Protective housing, glass; outer shell; sterile closure
151 Jacket, tubular
152 Bottom, plane
153 Supporting web
155 Inner wall
157 Supporting stub
159 Supporting ribs
161 O-ring
200 Skin
201 Skin surface
202 Epidermis
203 Horny layer (stratum corneum)
204 Keratinization and regeneration layer
205 Papillary and reticular layer (dermis)
206 Subcutis
207 Diameter of the detached skin surface (201)
210 Pool of injection solution
211 Inflow channel

What is claimed is:
1. Cylinder-piston unit (10) of a needle free injector, with at least one cylinder (20) for accommodating an injection solution, at least one piston (80), the improvement which comprises:
the cylinder (20) has a bottom portion (33), on which a discharge tube (54, 55) with a discharge nozzle (60) is arranged, the bottom portion (33) of the cylinder (20) has a cylinder front end face (46), an elastic adhesive disc (110), which is displaceable in the direction of a centre line (5) of the cylinder-piston unit (10) between an installation position (111) and an application position (112), is slidably arranged on the discharge tube (54, 55) and/or on the bottom portion (33), the bottom portion (33) has an annular web (51), which extends forwards in a continuation of an outer wall (32) of the cylinder (20), the annular web (51) has a cylindrical inner wall (52), the annular web (51) encloses a receiving space (53) for the elastic adhesive disc (110), the elastic adhesive disc (110) slideable within the receiving space (53), the elastic adhesive disc (110) in the installation position (111) having a first portion thereof occupying a front area of the receiving space (53) with the remainder of the receiving space (53) being unoccupied between the cylinder front end face (46) of the bottom portion (33) of the cylinder (20) and the elastic adhesive disc (110) and a second portion of the elastic adhesive disc (110) extending beyond the cylindrical inner wall (52), upon actuation of the at least one piston (80) the elastic adhesive disc (110) slips further into the receiving space (53), the elastic adhesive disc (110) has a front adhesive coating (121) affixed to a front end face (113) of the elastic adhesive disc (110) and directed away from the bottom portion (33), the front adhesive coating (121) for temporarily bearing with adhesive bonding to the skin (200) of a patient during injection of the injection solution in the application position (112) and a rear adhesive coating (129) affixed to a rear end face (115) of the elastic adhesive disc (110) and directed towards the cylinder front end face (46) of the bottom portion (33) of the cylinder (20), in the installation position (111), the discharge tube (54, 55) can be sealed off in the elastic adhesive disc (110), in the application position (112), the elastic adhesive disc (110) bears with adhesive bonding of the rear adhesive coating (129) on the cylinder front end face (46) of the bottom portion (33) of the cylinder (20), and in the application position (112), a front edge (61) of the discharge nozzle (60) lies in the plane of the front adhesive coating (121) or protrudes beyond this plane by at least 0.5 mm.

2. Cylinder-piston unit with adhesive disc according to claim 1, wherein the elastic adhesive disc (110) located in the installation position (111) is at a distance of at least one millimeter from the cylinder front end face (46) of the bottom portion (33) directed towards it.

3. Cylinder-piston unit with adhesive disc according to claim 1, wherein the elastic adhesive disc (110), is an elastomer body, which is elastic at least in the longitudinal direction parallel to the centre line (5) of the cylinder-piston unit (10).

4. Cylinder-piston unit with adhesive disc according to claim 1, wherein an outer wall (57) of the discharge tube (54, 55) is shaped cylindrically at least in part.

5. Cylinder-piston unit with adhesive disc according to claim 1, wherein the elastic adhesive disc (110) has a bore (122), which is closed by a sealing element (125).

6. Cylinder-piston unit with adhesive disc according to claim 1, wherein the adhesive bonding of the rear adhesive coating (129) has a greater adherence to the cylinder front end face (113) of the bottom portion (33) than the adherence of the front adhesive coating (121) to the skin (200) of a patient in the application position (112).

* * * * *